United States Patent
Kantor et al.

(10) Patent No.: US 6,837,468 B1
(45) Date of Patent: Jan. 4, 2005

(54) FRICTION CONTROL FOR ARTICULATING ARM JOINT

(75) Inventors: Arkady Kantor, Buffalo Grove, WI (US); James W. Kleinschmidt, Prospect Heights, IL (US)

(73) Assignee: Progeny, Inc., Buffalo Grove, IL (US)

( * ) Notice: Subject to any disclaimer, the term of this patent is extended or adjusted under 35 U.S.C. 154(b) by 0 days.

(21) Appl. No.: 10/250,024

(22) Filed: May 29, 2003

(51) Int. Cl.[7] .............................................. E04G 3/00
(52) U.S. Cl. ................................................. 248/278.1
(58) Field of Search .................... 248/276.1, 278.1, 248/280.11, 281.11, 282.1; 403/83, 84, 87, 94, 120, 93; 188/83, 71.1; 74/490.05, 490.06; 482/115; 439/15

(56) References Cited

U.S. PATENT DOCUMENTS

| | | | | |
|---|---|---|---|---|
| 3,593,952 A | * | 7/1971 | Smith | 248/214 |
| 3,669,089 A | * | 6/1972 | Swenson | 125/11.01 |
| 3,904,298 A | * | 9/1975 | Lindgren | 403/93 |
| 4,548,446 A | * | 10/1985 | Warshawsky | 439/13 |
| D290,500 S | * | 6/1987 | Makas et al. | D24/158 |
| 4,993,057 A | | 2/1991 | Runnells | |
| 5,116,180 A | * | 5/1992 | Fung et al. | 414/5 |
| 5,388,308 A | * | 2/1995 | Meeuwissen | 16/340 |
| 5,492,296 A | * | 2/1996 | Biber | 248/292.13 |
| D387,163 S | * | 12/1997 | Osthues et al. | D24/158 |
| 6,315,259 B1 | | 11/2001 | Kolb | |
| 6,626,806 B2 | * | 9/2003 | Stevens | 482/114 |

FOREIGN PATENT DOCUMENTS

GB   1 551 730 A   * 8/1979

* cited by examiner

*Primary Examiner*—Leslie A. Braun
*Assistant Examiner*—Kofi Schulterbrandt

(57) ABSTRACT

A friction control mechanism for an articulating arm including an arm, a pivot connector, an axial washer, and at least one set screw. An axial washer is placed around each side of a center aperture in the pivot connector. The pivot connector is connected to the arm with a pivot pin through the center aperture in the pivot connector and aligned holes in the first and second sides of the arm. At least one threaded hole is located adjacent the aligned hole in the first side of the arm. A set screw is placed through each threaded hole, making contact with the axial washer. This contact creates a friction force between the pivot connector and the axial washer, keeping the articulating arm from drifting away from its set position. The pivot connector may be connected to another device such as another arm or a machine such as an x-ray machine, or to another pivot connector.

12 Claims, 5 Drawing Sheets

FRICTION CONTROL FOR ARTICULATING ARM JOINT

BACKGROUND OF INVENTION

This invention relates generally to articulating arms for movably connecting a first body to a second body, specifically to a friction control mechanism for permitting close control of the friction at a joint of an articulating arm, allowing the articulating arm to hold the second body in a set position with respect to the first body after movement.

Articulating arms that extend between a first body and a second body are well known in the art. Dental x-ray machines, for example, often use such articulating arms. The dental x-ray machine often has an x-ray machine head that must be located next to the patient's jaw while in use. Further, it must maintain that position without being held there by an operator, so that the operator can move behind a screen so as to be protected from the x-rays when the machine is operating. When the x-ray machine is not in use, the x-ray machine head must be moved to a location that will not interfere with the rest of the dentist's duties. An articulating arm allows the x-ray machine head to be easily moved between these locations.

Another usage for such articulating arms is to moveably attach a machine to a remote input/output station while maintaining the orientation of the input/output station without being held by an operator. For example, an x-ray machine often has an output screen for providing information to the operator. The operator must be able to see the screen from a remote position where he or she is behind a shield and protected from the effects of the x-rays. The articulating arm maintains the orientation of the screen without being held there by the operator, while allowing the operator use both hands to operate x-ray controls. The operator can move the screen horizontally and vertically to a position where he or she can view it from the remote location. U.S. Pat. No. 6,315,259 issued to Kolb is an example of such an articulating arm.

One problem with existing articulating arms is that they tend to permit drift, so that the piece of equipment being held by the arm loses its set position after the operator moves the equipment to the desired location and releases it. This is a particular problem with articulating arms used with dental x-ray machines. To take dental x-rays, the operator moves the x-ray machine head, attached to an articulating arm, to the desired location next to the patient's jaw, and then must leave the room to activate the x-ray machine. Before the operator is able to activate the x-ray machine, the articulating arm attached to the x-ray machine may lose its set position, causing the x-ray machine head to be in a different position than the operator intended. As a result, an unintended area of the patient's jaw may have been x-rayed, and the operator may have to repeat the x-ray. This wastes both the operator's and the patient's time, as well as potentially exposing the patient to unnecessary x-rays.

This invention relates to improvements to the products described above, and to solutions to some of the problems raised or not solved thereby.

SUMMARY OF INVENTION

The present invention provides a friction control mechanism for the connecting joints in an articulating arm, so as to stop the piece of equipment held by the articulating arm from drifting away from its set position. The friction control mechanism includes a pivot connector attached to an arm with a pivot pin, an axial washer placed around the pivot pin and between the arm and the pivot connector, and two set screws threaded through the arm. The set screws are positioned and oriented so that they bite into the axial washer, generally preventing relative movement between the set screws and the axial washer, and creating a friction force between the axial washer and the pivot connector. This friction force is sufficient to hold the arm in its set position, preventing any drift. The set screws can be adjusted to control the level of the friction force between the axial washer and the pivot connector.

As part of an articulating arm, the pivot connector may be connected to another device, such as another part of the arm, a machine such as an x-ray machine, or another pivot connector for connection to another arm. Each joint in the articulating arm may have such a friction control mechanism.

Various other features, objects, and advantages of the invention will be made apparent to those skilled in the art from the following detailed description, claims, and accompanying drawings.

DETAILED DESCRIPTION

Figure 1:
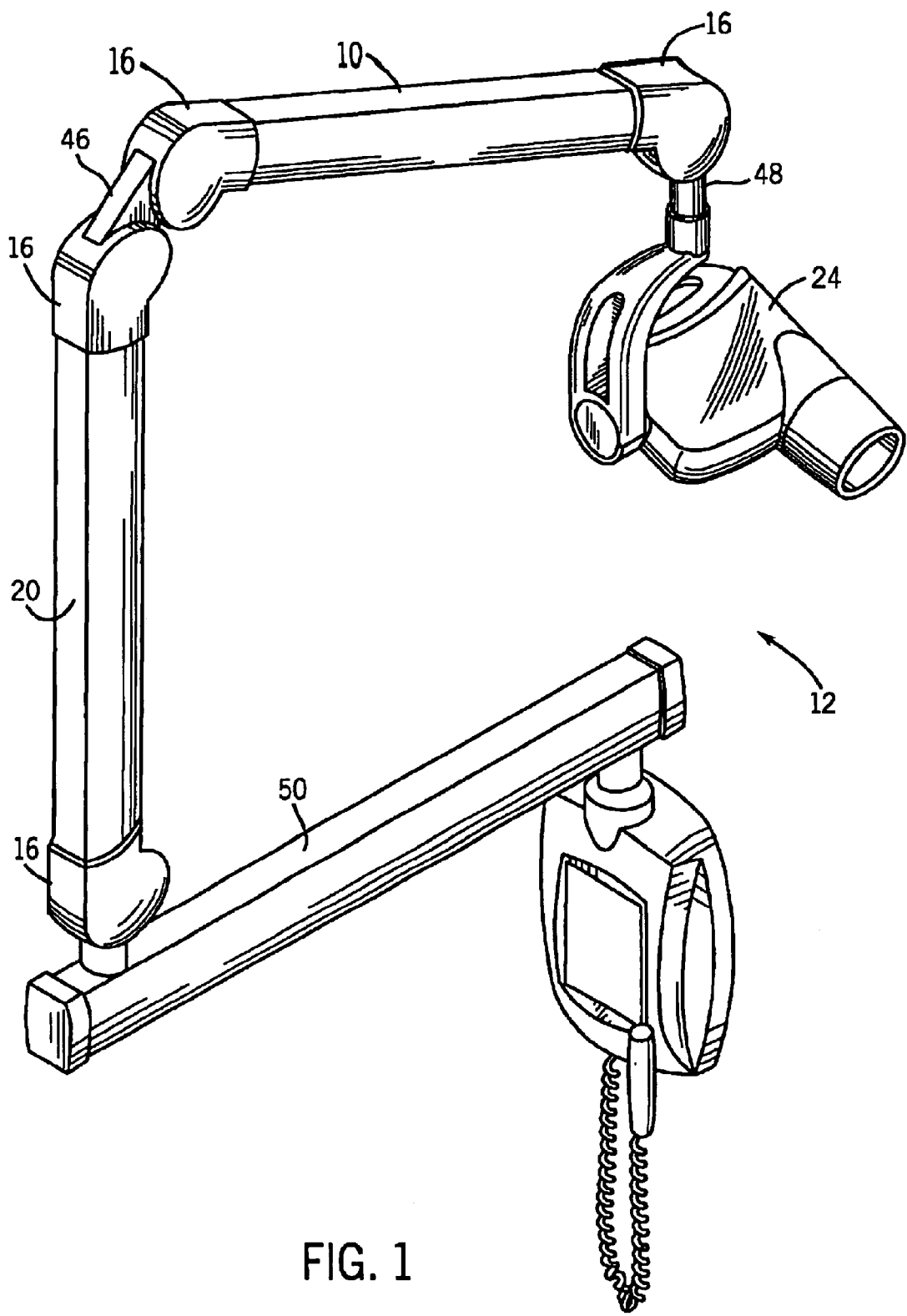
FIG. 1 is a perspective view of an articulating arm constructed according to a preferred embodiment of the invention, applied to hold the x-ray head of a dental x-ray machine.

The invention is used to prevent drift in an articulating arm assembly 20 used in connection with a dental x-ray machine 12 as shown in FIG. 1. One or more of the joints 16 in the articulating arm assembly 20 may include the structure provided by the invention, improving the ability of the joints 16 to maintain a set position. As a result, the x-ray machine head 24 will stay in the proper position and x-ray the correct area of the patient's jaw.

Figure 2:
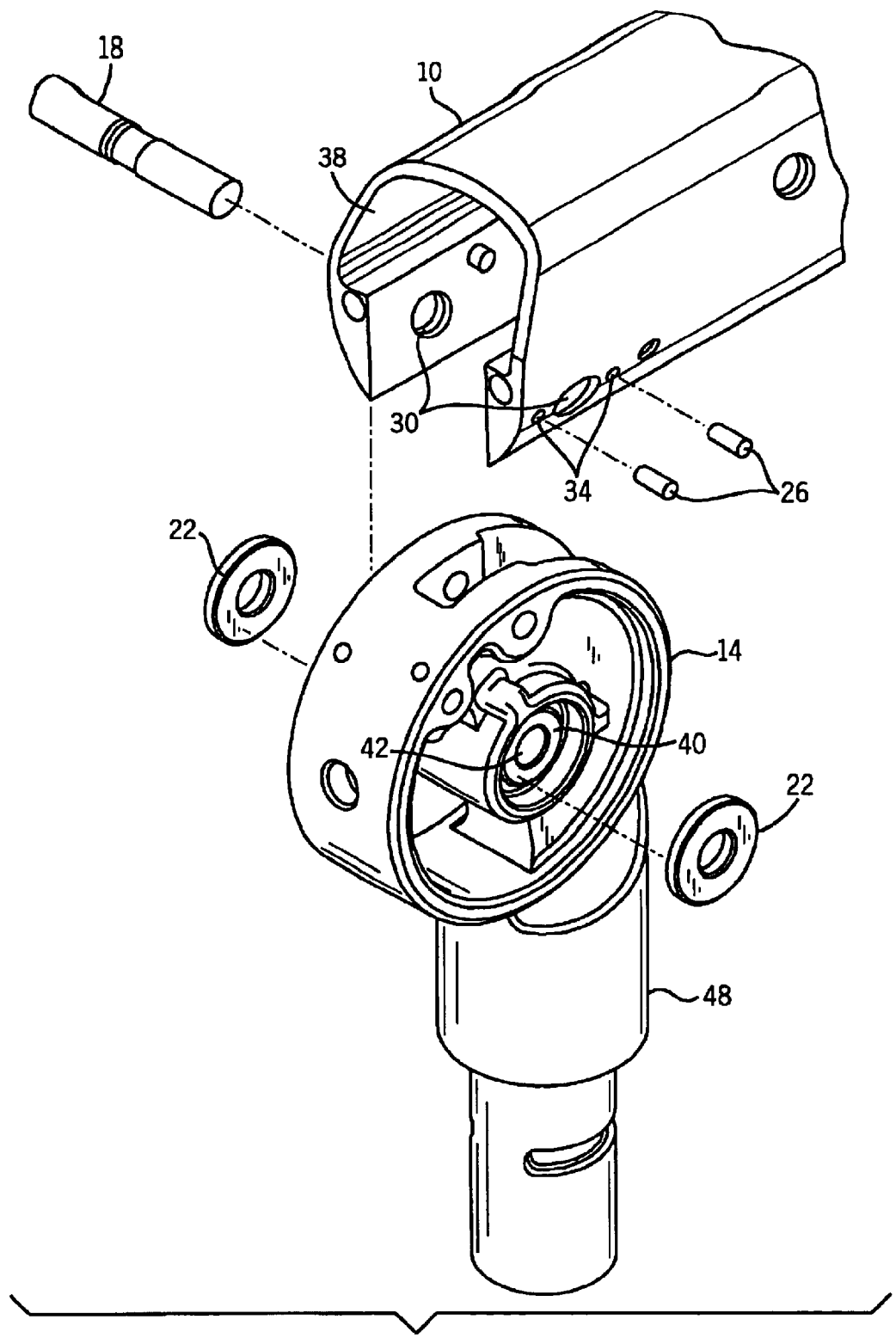
FIG. 2 is an exploded view of one joint of the articulating arm shown in FIG. 1, illustrating the relationship of the component parts.

As shown in FIG. 2, a preferred embodiment of the invention includes an arm 10, generally hollow, at least at the end where the joint is to be formed. One preferred cross-sectional shape for the arm 10, as shown in FIG. 2, is that of a U-shape. In that form, the arm 10 includes two sides 38. A pivot connector 14 is positioned between the sides 38. The pivot connector 14 has a center aperture 42 and is fastened to the arm 10 by means of a pivot pin 18. The pivot pin 18 is positioned through aligned holes 30 in sides 38, and the center aperture 42 of the pivot connector 14. Axial washers 22 are applied around each end of the pivot pin 18, between the sides 38 of the arm 10, and outside the pivot connector 14. Set screws 26 are threaded through threaded holes 34 formed in the sides 38, which threaded holes are offset from the aligned holes 30. As each set screw 26 is threaded into the threaded holes 34, it bites into the axial washer 22, thereby substantially preventing relative motion between the arm 10 and the washer, and exerting an inward force on the washer, increasing the pressure by which the washer contacts a flat surface 40 provided for that purpose. The pressure between the washer 22 and the flat surface 40 creates a friction force between the pivot connector 14 and the arm 10. This friction force controls how easily the arm 10 moves relative to the pivot connector 14. The pivot connector 14 has an attachment portion 48 to facilitate attachment to other parts, such as another arm 50 (FIG. 1) or a an x-ray head 24 (FIG. 1).

Figure 3:
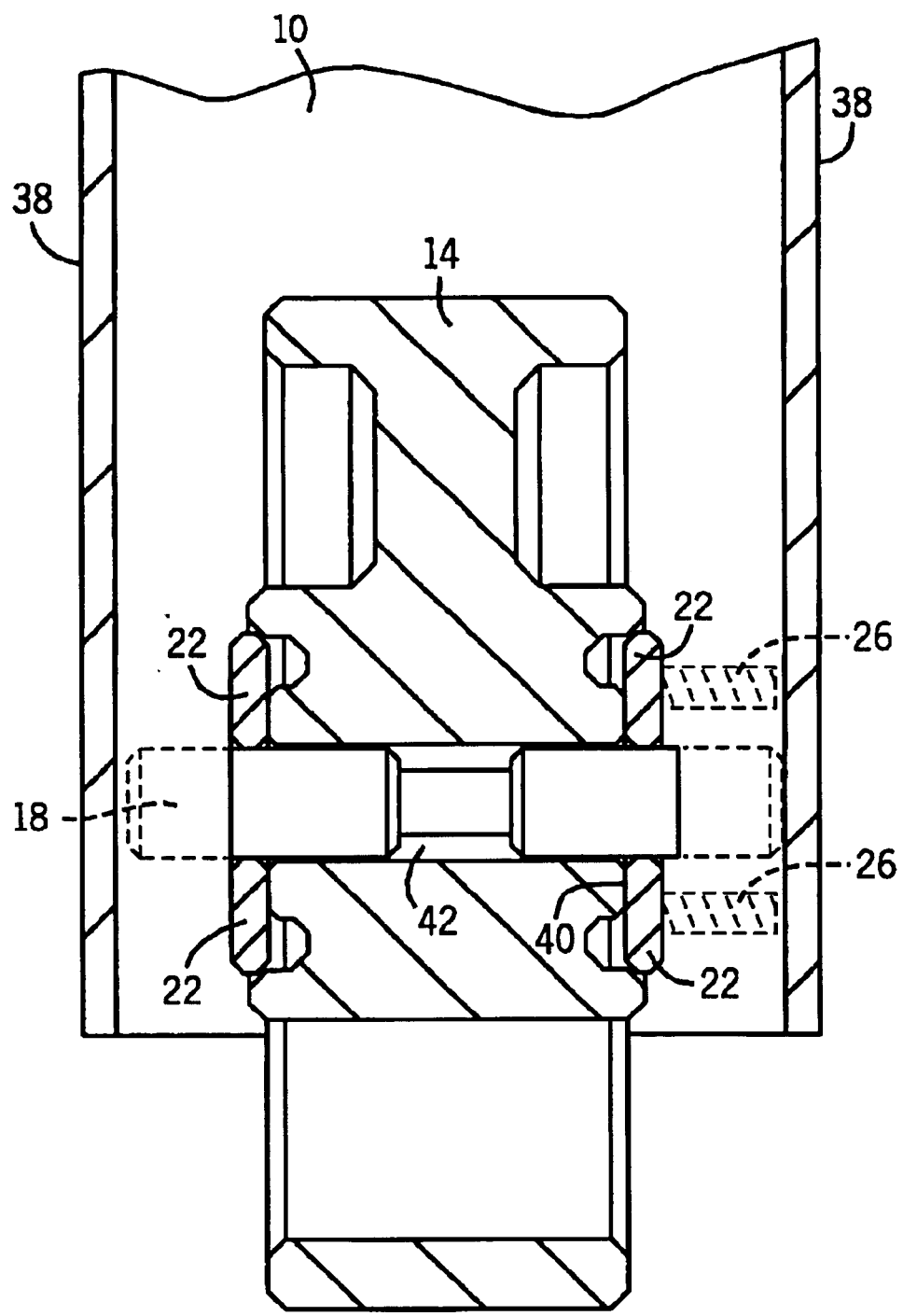
FIG. 3 is a cross-sectional view of the joint shown in FIG. 2, taken along line 3—3 thereof.

The benefit of the invention can be more clearly seen by reference to FIG. 3. As there shown, the pivot pin 18 is placed through the center aperture 42. The axial washers 22 are fitted around each end of the pivot pin 18 and between the sides 38 of the arm 10 and the flat surface 40 of pivot connector 14. The set screws 26 are shown making contact with the axial washers The contact between the set screws 26 and the axial washer 22 prevents relative movement therebetween, and creates a friction force between the pivot connector flat surface 40 and the axial washer 22. The set screws 26 can then be adjusted to control the degree of friction force necessary to prevent drift.

Figure 4:
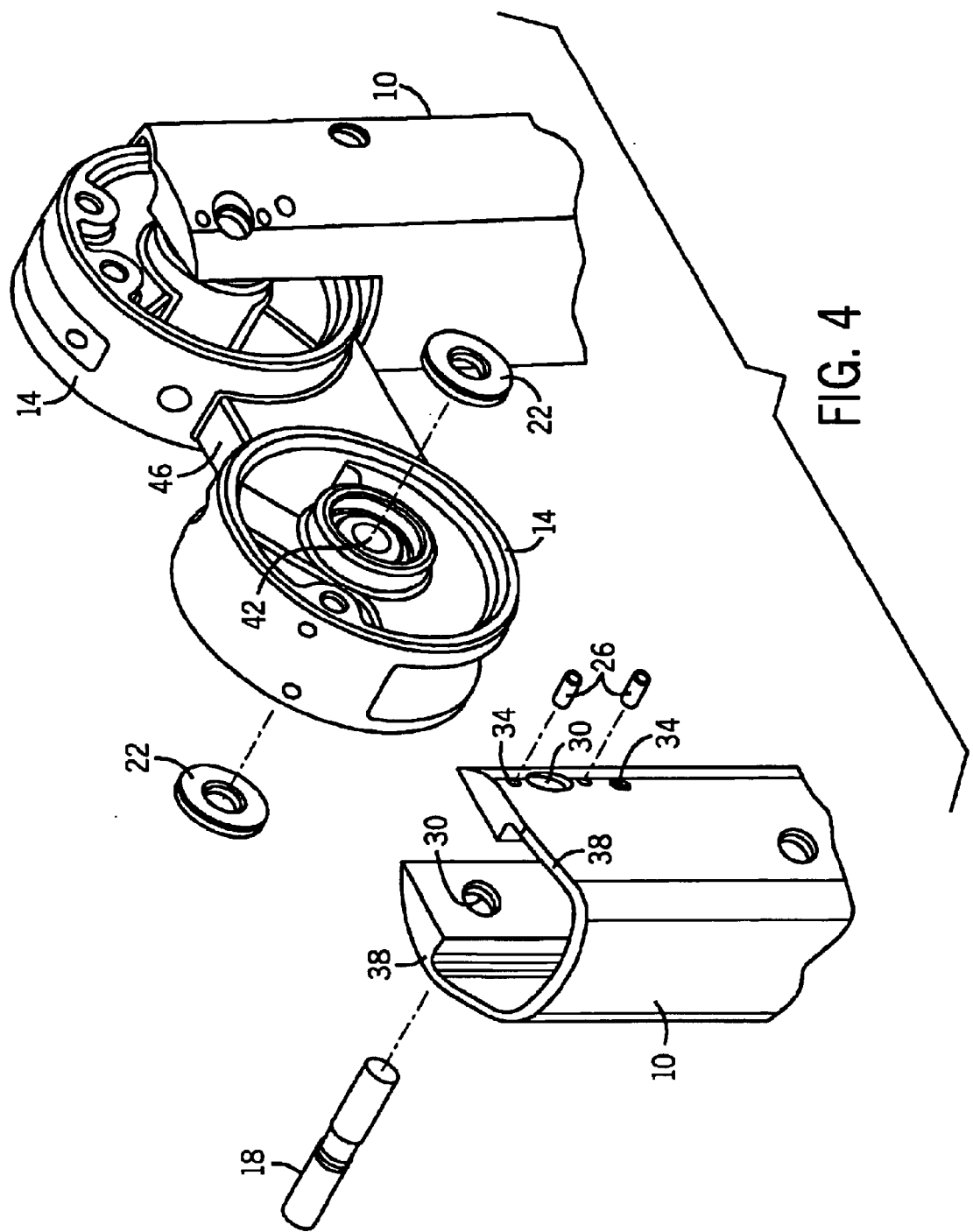
FIG. 4 is an exploded view of a joint of an articulating arm, constructed according to an alternative embodiment of the invention.1.
Figure 5:
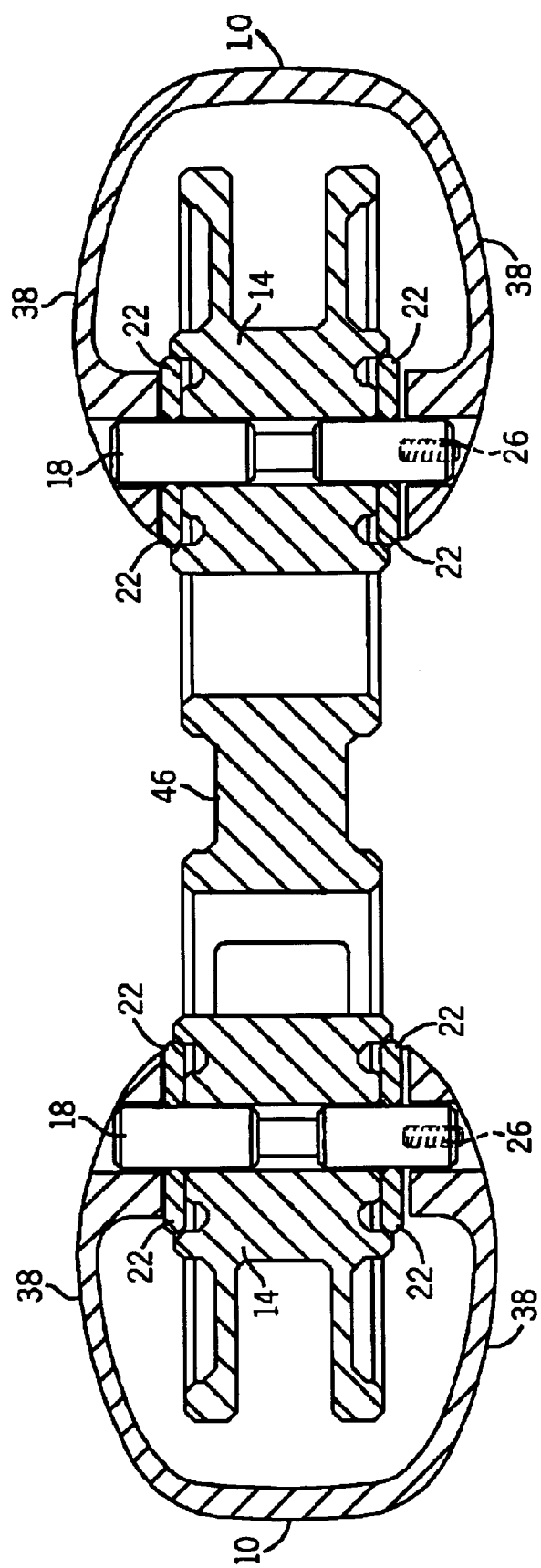
FIG. 5 is a sectional view of the embodiment of the invention shown in FIG. 4, taken along line 5—5 thereof.

A second embodiment of the invention may be used with joints requiring two pivot connectors as illustrated in FIGS. 4 and 5, FIG. 4 being an exploded view and FIG. 5 being a cross-sectional view. As there shown, the pivot connector 14 is connected to a second pivot connector 14 by a coupler 46. The second pivot connector 14 is connected to a second arm 10 by a second pivot pin 18. An axial washer 22 is applied about each end of the pivot pin 18, between the sides 38 of the second arm 10 and the flat surface 40 of the second pivot connector 14. Two set screws 26 are threaded through two threaded holes 34, contacting the axial washer 22.

The pivot connector is preferably formed of cast aluminum and the axial washers are preferably formed of stainless steel. Other material combinations are possible, but many do not work as well. For example, both aluminum-on-aluminum and aluminum-on-brass tend to bond and score or result in excessive wear.

While the invention has been described with reference to preferred embodiments, it is to be understood that the invention is not intended to be limited to the specific embodiments set forth above. It is recognized that those skilled in the art will appreciate certain substitutions, alterations, modifications, and omissions may be made without parting from the spirit or intent of the invention. Accordingly, the foregoing description is meant to be exemplary only, the invention is to be taken as including all reasonable equivalents to the subject matter of the invention, and should not limit the scope of the invention set forth in the following claims.

What is claimed is:

1. A friction control mechanism for an articulating arm, the mechanism comprising:
    an arm having a top portion, a first side portion and a second side portion, the first side portion and the second side portion, each side portion having a hole aligned with a respective hole in the opposite side portion;
    a pivot connector positioned between the first side portion and the second side portion of the arm, the pivot connector having a center aperture;
    a pivot pin having a first end and a second end, the pivot pin connecting the pivot connector to the arm by the positioning of the pivot pin through the center aperture of the pivot connector and through the aligned holes on the first and second side portions;
    a first axial washer applied about the first end of the pivot pin and positioned between the first side portion of the arm and the pivot connector;
    a second axial washer applied about the second end of the pivot pin and positioned between the second side portion of the arm and the pivot connector;
    at least one set screw threaded through one of the two side portions of the arm, the set screw contacting the first axial washer and providing control of a friction force between the pivot connector and the first axial washer.

2. The friction control mechanism of claim 1, wherein the pivot connector is formed of aluminum, and wherein the first axial washer is formed of stainless steel.

3. The friction control mechanism of claim 1, wherein the pivot connector is connected to a second pivot connector.

4. The friction control mechanism of claim 3, further comprising a second arm, the second arm having a top portion, a first side portion and a second side portion, the first side portion and the second side portion having a pair of aligned holes;
    the second pivot connector positioned between the first side portion and the second side portion of the second arm, the second pivot connector having a center aperture;
    a second pivot pin having a first end and a second end, the second pivot pin connecting the second pivot connector to the arm, the second pivot pin positioned through the center aperture of the second pivot connector and through the aligned holes on the first and second side portions of the second arm;
    a third axial washer applied about the first end of the second pivot pin and positioned between the first side portion of the second arm and the second pivot connector;
    a fourth axial washer applied about the second end of the second pivot pin and positioned between the second side portion of the second arm and the second pivot connector; at least one set screw threaded through the first side portion of the second arm, the set screw contacting the third axial washer to control friction force between the pivot connector and the third axial washer.

5. The friction control mechanism of claim 1, wherein the pivot connector is moveably connected to an x-ray machine head.

6. The friction control mechanism of claim 1, wherein the pivot connector has a cylindrical lower portion for connection to another device.

7. A friction control mechanism for an articulating arm, the mechanism comprising:
    an arm having a top portion, a first side portion and a second side portion, the first side portion and the second side portion having a pair of aligned holes;
    a pivot connector positioned between the first side portion and the second side portion of the arm, the pivot connector having a center aperture;
    a pivot pin having a first end and a second end, the pivot pin connecting the pivot connector to the arm, the pivot pin positioned through the center aperture of the pivot connector and through the aligned holes on the first and second side portions;
    a first axial washer positioned around the first end of the pivot pin and between the first side portion of the arm and the pivot connector;
    a second axial washer positioned around the second end of the pivot pin and between the second side portion of the arm and the pivot connector;

at least one set screw threaded through the first side portion of the arm, the set screw contacting the first axial washer to control friction force between the pivot connector and the first axial washer;

a second arm having a top portion, a first side portion and a second side portion, the first side portion and the second side portion having a pair of aligned holes;

a second pivot connector positioned between the first side portion and the second side portion of the second arm, the second pivot connector having a center aperture;

a second pivot pin having a first end and a second end, the second pivot pin connecting the second pivot connector to the second arm, the second pivot pin positioned through the center aperture of the second pivot connector and through the aligned holes on the first and second side portions of the second arm;

a third axial washer positioned around the first end of the second pivot pin and between the first side portion of the second arm and the second pivot connector;

a fourth axial washer positioned around the second end of the second pivot pin and between the second side portion of the second arm and the second pivot connector;

at least one set screw threaded through the first side portion of the second arm, the set screw contacting the third axial washer to control friction force between the pivot connector and the third axial washer; and, the first pivot connector connected to the second pivot connector.

8. The friction control mechanism of claim 7, wherein the pivot connector is formed of aluminum, and wherein the first axial washer and the third axial washer are formed of stainless steel.

9. A method for assembling a friction control mechanism for an articulating arm, comprising:

placing a pivot connector between first and second sides of an arm;

placing an axial washer on each side of a center aperture in the pivot connector, within the sides of the arm;

connecting the pivot connector to the arm with a pivot pin through the center aperture on the pivot connector and through aligned holes on the first and second sides of the arm and through the washers;

threading at least one set screw through the first side of the arm until the set screw contacts the axial washer and causes the axial washer to contact the pivot connector.

10. The method of claim 9, further comprising the step of adjusting the set screw to control the degree of friction force between the pivot connector and the arm.

11. The method of claim 9, further comprising the step of connecting the pivot connector to an x-ray machine head.

12. The method of claim 9, further comprising the step of connecting the pivot connector to a second pivot connector.

* * * * *